United States Patent [19]

Rubinstein

[11] Patent Number: 4,944,920

[45] Date of Patent: Jul. 31, 1990

[54] NOVEL METHOD TO TREAT BLOOD

[75] Inventor: Alan I. Rubinstein, Los Angeles, Calif.

[73] Assignee: University of Southern California, Los Angeles, Calif.

[21] Appl. No.: 316,604

[22] Filed: Feb. 27, 1989

Related U.S. Application Data

[63] Continuation of Ser. No. 892,058, Aug. 1, 1986, abandoned, which is a continuation-in-part of Ser. No. 838,253, Mar. 10, 1986, abandoned.

[51] Int. Cl.$^5$ .................... A61L 2/18; C07K 15/06
[52] U.S. Cl. ........................ 422/37; 422/28; 424/533; 435/2; 435/288; 514/833; 530/385
[58] Field of Search ............ 424/101; 422/28, 37; 435/2, 288; 530/385; 514/833

[56] References Cited

U.S. PATENT DOCUMENTS

| | | | |
|---|---|---|---|
| Re. 27,359 | 5/1972 | Ilg | 424/101 X |
| Re. 31,799 | 12/1984 | Alliger | 422/28 X |
| 1,556,120 | 10/1925 | Mills | 424/101 X |
| 2,134,679 | 11/1928 | Allen | 422/28 X |
| 2,897,123 | 7/1959 | Singher | |
| 3,031,378 | 4/1962 | Ishidate | |
| 3,041,242 | 6/1962 | Barr et al. | 424/101 |
| 3,100,737 | 8/1963 | Auerswald et al. | 424/101 |
| 4,084,747 | 4/1978 | Alliger | 422/28 X |
| 4,314,997 | 2/1982 | Shanbrom | 424/101 |
| 4,481,189 | 11/1984 | Prince | 424/101 |
| 4,632,980 | 12/1986 | Zee et al. | 424/101 X |

OTHER PUBLICATIONS

Alcide Corporation Product Literature on LD TM Disinfectant, (1985), 5 pages.
Gallo et al., Science, vol. 224, 4 May 1984, pp. 500-503.
Sarin et al., J. Clin. Immunology, vol. 4, No. 6, pp. 415-423.
Wong-Staal et al., Nature, vol. 317, 3 Oct. 1985, pp. 395-402.
Sarin et al., NE J. Medicine, Nov. 28, 1985, p. 1416.

*Primary Examiner*—Robert J. Warden
*Assistant Examiner*—Jill Johnston

[57] ABSTRACT

It is well known that the transfusion of human blood and blood components carriers with it a substantial risk of transmission of AIDS and many other diseases. This disclosure describes a method of disinfecting red blood cells to make them safer for human transfusion, while maintaining their biologic activity. A sterilizing solution is prepared from, e.g., a commercially available disinfectant (LD TM Alcide Corporation) containing primarily lactic acid and sodium chlorite. Normal saline solution is used as diluent instead of distilled water. The red cells are exposed to the disinfectant for a time sufficient to inactivate or reduce the infectivity of disease agents. The normal-saline environment prevents or deters hemolysis. The blood cells are then washed with normal saline solution until the disinfectant concentration is insignificant. The blood is then safe for human transfusion.

20 Claims, No Drawings

NOVEL METHOD TO TREAT BLOOD

This is a continuation of co-pending application Ser. No. 06/892,058 filed on Aug. 1, 1986, now abandoned, which is a continuation-in-part of Ser. No. 838,253, filed Mar. 10, 1986, now abandoned.

BACKGROUND

1. Field of the Invention

This invention relates generally to processing of blood substances; and more particularly to disinfecting red blood cells and subsequently removing the disinfectant from the red blood cells.

This processing is designed to inactivate or greatly reduce the activity of certain harmful contaminants, thus rendering the blood cells safe for human therapeutic use. Such harmful contaminants include, but are not limited to, several blood-borne viruses and other microorganisms that are known to cause or suspected of causing AIDS, the various known forms of viral hepatitis, cytomegalovirus, and Epstein-Barr virus.

2. Prior Art

Even though human blood is supplied for transfusion purposes very commonly, there has been no way to guarantee the safety of human blood for transfusion. There is thus an important need to make human blood a safe product.

Transfusion of human blood—particularly its red-blood-cell component—carries a well-known risk for transmitting viruses, including the hepatitis B virus; the non-A, non-B hepatitis virus or viruses; and the HTLV-III virus. HTLV-III is a human retrovirus which has been implicated in AIDS (see Gallo, R. C. et al.).

Detection and isolation of cytopathic retroviruses (HTLV-III) from patients with AIDS, and certain members of groups at high risk for AIDS, have been frequently reported. One such report appears in *Science* 1984; 224:500–3.

For further corroboration of these findings, see Sarin, P. S. et al., Human T-Lymphotrophic Retroviruses in Adult T-cell Leukemia-Lymphoma and Acquired Immune Deficiency Syndrome, *J. Clinical Immunol.* 1984; 4:415–23; and Wong-Staal, F., Gallo, R. C., Human T-Lymphotrophic Retroviruses, *Nature* 1985; 317:395–402.

Development of new disinfectants and automated cell washers (e.g., the IBM Cell Washer) that can wash red blood cells has created new possibilities for sterilizing human blood components to allow safe transfusion. In particular, Sarin et al. have reported that a laboratory disinfectant composed of approximately 0.23 percent sodium chlorite and 1.26 percent lactic acid (LD TM Alcide, Norwalk, Conn.) at a dilution of 1:200 or less can completely inactivate the HTLV-III/HIV virus (see *New Engl. J. Med.* 1985; 313:1416). That disinfectant corresponds to the teachings of Howard Alliger's U.S. Pat. No. 4,084,747 and Re. No. 31,779, whose teachings are hereby incorporated by reference.

It has not been practical, however, to treat human blood with disinfectant, as this process has been too toxic to red blood cells. In particular, hemolysis resulted.

Thus no process to eliminate or lessen the transmission of harmful contaminants in transfusion of human blood has been available.

SUMMARY OF THE DISCLOSURE

I have now found that units of red blood cells, and potentially units of whole blood, can be safely and economically sterilized while in a collection bag. I have found that for red blood cells this can be accomplished quickly and easily, with materials readily available.

My invention is a method for treating a blood substance comprising red blood cells, to inactivate or greatly reduce the activity therein of certain harmful contaminants. The blood substance may itself be red blood cells.

The harmful contaminants of concern may include HTLV-III or any other AIDS-causing agents; or cytomegalovirus or Epstein-Barr virus, or any of several forms of hepatitis agent, or any other virus or any other microorganism. Contaminants of concern may include combinations of any or all of those listed here.

Some specific hepatitis agents of interest may be mentioned, though I do not wish to limit applications of my invention to them. Agents of interest include hepatitis A virus, hepatitis B virus, delta hepatitis virus, the hepatitis agent or agents known as "non-A, non-B virus or viruses," and any other agent of blood-transmitted hepatitis that may occur.

My invention itself includes at least two steps. The first step is adding disinfectant to the blood substance. The second step, which is performed after the first, is removing the disinfectant from the red blood cells.

The foregoing may be a description of my invention in its most general or broadest form. As will be appreciated, however, I prefer to practice the method with certain advantageous detailed steps not mentioned above.

For example, before the adding step, I prefer to prepare the disinfectant by diluting lactic acid and sodium chlorite in normal saline. I also prefer that the adding step include putting the disinfectant into an automated or semiautomated machine such as a cell washer.

In addition I prefer to maintain the disinfectant in contact with the blood substance for an extended time period. This should be done between the adding and removing steps.

I prefer to separate the red blood cells from any other constituents of the blood substance that may be present, at some time before the removing step. I prefer to perform this separation before the adding step.

My procedure is practical, useful, easy, and economical. Its advantages particularly include eliminating, or at the very least strongly reducing, transmission of the previously mentioned harmful contaminants in blood transfusions.

In particular, the use of diluent normal saline prevents or strongly deters hemolysis and thereby renders my process invention noninjurious to the red blood cells. This result is in marked contrast to previous unsuccessfully attempted procedures.

Furthermore, I have found that my process leaves substantially intact certain blood constituents recognized as indicators of normal red cell activity. In short, my invention disinfects red blood cells without damaging them.

All of these principles and advantages of my invention will be more fully appreciated upon consideration of the following detailed description.

DETAILED DESCRIPTION OF PREFERRED EMBODIMENTS

1. Sterilization Technique

In a preferred form of my invention, I disinfect certain components of human blood as follows. First, units of human red blood cells are separated from the plasma.

Then they are exposed for an extended period of time to a disinfectant solution composed of approximately 0.23 percent sodium chlorite and 1.26 percent lactic acid, diluted with normal saline (that is, a 0.9-percent aqueous solution of sodium chloride) up to 1:200 or higher.

By "extended period of time" I mean to encompass, for example, a relatively very short period such as a few seconds, as well as a relatively longer time such as a few or many minutes. Following exposure of the unit of red blood cells to the disinfectant, the disinfectant is removed from the red blood cells. Such removal advantageously includes washing, with or without the aid of automation.

If an automated cell washer (such as an IBM Cell Washer) is used, it may be programmed to give the disinfectant a 200-fold dilution of its standard-use dilution. It appears that dilutions over as broad a range as 1:2 to 1:2000 may be usefully encompassed within my invention, although as already stated I prefer 1:200.

The washer may further be programmed to next mix the disinfectant with the red blood cells for a few seconds. The washer may also be programmed to then wash the cells automatically.

Disinfectant composition, as well as disinfection times, may be varied without departing from the scope and spirit of my invention. Automation increases the utility of my invention, since through the use of automation red blood cells may be washed rapidly and the invention practiced on a production scale.

More specifically, LD ™ disinfectant solution was obtained from Alcide Corporation in two parts, a "base" and an "activator." These materials are understood to include sodium chlorite and lactic acid.

The two parts were mixed with diluent in accordance with the manufacturer's instructions, with one crucial exception: normal saline was substituted for the distilled water specified by the manufacturer. Thus, one part LD base was mixed with ten parts normal saline. One part activator was added and the solution further diluted with normal saline to an overall dilution of 1:200.

In the final disinfectant solution the concentrations of sodium chlorite and lactic acid were each below two percent. The pH of the solution was adjusted to a value between four and five.

Two aliquots of red blood cells from a unit of red blood cells supplied by the American Red Cross were washed three times in normal saline. One aliquot of the washed red blood cells was held in a container labeled "EXP" (experiment).

To this container, which was approximately one-third full, was added the above-described disinfectant in an amount to fill the container. The contents of the container were mixed, and the mixture allowed to stand for approximately ten to fifty seconds.

Then the cells were washed in normal saline four times and resuspended in normal saline. No hemolysis was observed in the disinfected cells.

The control aliquot of red blood cells was washed in identical fashion, but no disinfectant was added. The control, too, was free from hemolysis.

To verify that the red blood cells treated with the disinfectant were still viable and thus suitable for transfusion, assays were performed on them as described in the following section. As detailed therein, the oxygen transfer capability and enzymatic activity of two representative constituents of the disinfected red blood cells were found to be substantially intact.

Based upon these several tests, I believe that the integrity of my process is established. After washing in normal saline, the red blood cells are ready for transfusion—safe from transmitting the various harmful contaminants mentioned earlier, and others.

2. Verification of Blood-Cell Viability

The disinfected and washed cells were stored in normal saline for several days at approximately four degrees Celsius, followed by incubation at thirty-seven degrees Celsius in a solution of glucose, inorganic phosphorus, potassium, and magnesium.

The cells were then assayed for 2,3 DPG and ATP. The methodology used in these assays has been described (see Keith, A. S.: Reduced nicotinamide adenine denucleotide-linked analysis of 2,3 diphosphoglyceric acid: spectrophotometric and fluorometric procedures, *General Lab. Clin. Med.*, 1971; 77:470; see also Worek, Gruber, Bergmeyer: Adenosine, 5, triphosphate, determination with 3-phosphoglycerate kinase, in Bergmeyer, H. U. [ed.]: *Methods of Enzymatic Analysis*, vol. 4, N.Y. Academic Press, 1974, p. 2097).

The presence of 2,3-diphosphoglyceric acid (DPG) phosphatase activity in preparations of monophosphoglycerate mutase (PGM) from muscle and other sources has been noted by several workers. Lowry and coworkers exploited this presence to measure the very low levels of 2,3-DPG in acid extracts of brain tissue.

They measured a product of the phosphatase activity, 3-phosphoglyceric acid (3-PGA), fluorometrically. Lowry's group used a reduced nicotinamide adenine dinucleotide (NADH)-linked reaction.

In that reaction 3-PGA was converted stoichiometrically to glyceraldehyde 3-phosphate (G-3P) by phosphoglycerate kinase (PGK) and glyceraldehyde 3-phosphate dehydrogenase (G3PD). I have modified this fluorometric procedure for measurement of the much higher concentrations of 2,3-DPG in red blood cells.

Rose has reported that in red blood cells 2,3-DPG phosphatase is stimulated by both pyrophosphate and 2-phosphoglycolic acid, a property which is shared by the phosphatase activity in muscle PGM. She has devised a spectrophotometric assay for 2,3-DPG with the use of 2-phosphoglycolate and PGM, converting the 3-PGA formed to lactate.

The fluorometric and spectrophotometric assays for 2,3-DPG described below are those which proved most versatile and reliable. They represent a composite of the methods of Lowry and coworkers, Rose and Liebowitz, and Czok and Eckert.

Laboratory Technique

Imidazole (grade III), reduced glutathione (GSH), hydrazine sulfate solution (No. 750-3), and 2-phosphoglycolate were obtained. Distilled water was passed through a mixed-bed deionizer, which greatly reduced the fluorescence of the water.

Preparation of samples: Customarily, one volume of whole blood is added to two volumes of ice-cold six percent (w/v) perchloric acid (PCA); it is mixed thoroughly and left on ice for at least fifteen minutes. The brown, denatured protein is separated by centrifugation at 27,000 gravities for twenty minutes at two degrees Celsius. The clear supernatant is then neutralized with approximately one sixth volume of 2M $KHCO_2$.

Spectrophotometric assay: All reagents are prepared as stock solutions and stored frozen, except imidazole and hydrazine, which are stored at room temperature. Reactions are performed at twenty-five to twenty-eight degrees Celsius (without temperature control) in an automatic recording spectrophotometer in quartz semimicrocuvettes with one centimeter path lengths at 340 millimicrons.

For normal whole blood, neutral PCA extract (one-tenth milliliter) is added to one-milliliter aliquots of the reaction mixture. The volume of extract can be increased to at least three-tenths milliliter without affecting the reaction mixture.

The combined solution of G3PD and PGK (in four microliters) is added after all the 3-PGA and 1,3-DPG has reacted (usually they are undetectable), the absorbance at 340 millimicrons is determined at PGM (in five microliters) is added. The reaction normally goes to completion in fifteen to twenty minutes—but this should be determined for each new set of reagents, as the phosphatase activity of different lots of PGM varies slightly.

The blank cuvette contains distilled water instead of PCA extract. Blanks containing PCA extract, but no enzymes, are usually identical, but this should be verified periodically. When 2-mercapethanol was substituted for GSH, sporadically high blanks (0.03 to 0.04 O.D. units per ten minutes) were noted in the presence of neutral PCA extracts of whole blood without any added enzymes.

Fluorometric assay: A sample size of PCA extract (two to five microliters) is employed depending on the hematocrit of the sample. Samples and standards are added with the same selected micropipette. The reaction is complete in five minutes.

Calculations: 2,3-DPG concentration is derived by determining the difference in absorbance at 340 millimicrons before and after adding PGM, using an extinction coefficient of 6.22 O.D. units per millimole of NADH. The value is corrected for the reagent blank (usually less than 0.010 O.D. units). In the fluorometric assay, the change in NADH fluorescence is compared with that of a 2,3 Def solution which has been standardized spectrophotometrically.

There is a significant deviation from linearity in the absence of hydrazine when the initial concentration of 2,3-DPG approaches that of the available NADH. The obligatory liberation of inorganic phosphate from 2,3-DPG adversely affects the final ratio of 1,3-DPG to G-3-P so that G-3-P must be trapped with hydrazine, unless a large stoichiometric excess of NADH is employed.

Potency of the hydrazine solution should be verified periodically. This can be done by checking linearity against a standard curve.

The half-time of the fluorometric assay is normally less than one minute. Because of its great sensitivity, such an assay is readily used to measure very low concentrations of 2,3-DPG, such as might occur during storage of blood or in vitro experiments. The accuracy of this method is determined largely by the quality of the micropipettes and the skill of the technician in handling them.

Specificity: Adding PGM to the system results in the conversion of both 2,3-DPG and 2-DPA to 3-PGA. In normal blood, the concentration of 2-PGA is 300 times less than that of 2,3-DPG; it can be ignored. Where these compounds are present in more nearly equal concentrations, however, as in most tissues, discrimination may be more important.

The assay can be modified so that an approximation of 2-PGA content can be obtained by adding PGM (five milligrams per milliliter) without phosphoglycolate after 3-PGA has reacted. Under these conditions, 2-PGA will be rapidly converted to 3-PGA, while 2,3-DPG will react very slowly.

Selective activation of the phosphatase with phosphoglycolate will then measure 2,3-DPG. This modification requires fluorometric measurements of NADH for sufficient sensitivity at the low levels of 2-PGA usually present in tissues.

Methodology Preference

The advantages of this method are several. Its most important aspect is that it is an "endpoint" assay rather than a rate assay. The assay methods which relate 2,3-DPG concentration to its catalytic effect on the PGM reaction involve rate measurements, which are much more likely to be affected by minor variations in assay conditions.

"Rate" in these methods is often determined by an initial reading followed after one time interval by a single additional reading, and assuming linearity. Any deviations from linearity among different samples will therefore go undetected. Furthermore, the calculations depend on a calibration curve for a standard of known purity.

The "endpoint" assay, on the other hand, may be read at any convenient time after going to completion, provided that the blank cuvette is read at a similar interval. The calculations are based on the molar extinction coefficient of NADH when determined spectrophotometrically, and thus they do not depend on a standard curve.

If greater sensitivity is required, the fluorometric assay can be used. No fractionation of the extracted material is required, as it is in the total phosphate and chromotrophic acid methods.

The specificity, although not absolute because of the coreaction of 2-PGA, is entirely adequate for most red-cell applications, in which the 2-PGA concentration is negligible. Selective activation of 2,3-PGA activity by phosphoglycolate after 2-PGA has reacted can improve the specificity of the assay.

The "backward" reaction to G-3-P is more versatile than the "forward" reaction to lactate. Concentrations of 3-PGA and 2-PGA are usually negligible compared with that of 2,3-DPG.

Pyruvate on the other hand, may accumulate significantly under certain experimental conditions, and the initial lactate dehydrogenase reaction may then exhaust much of the NADH. Furthermore, at very low concentrations of 2,3-DPG, the coreaction of 2-PGA concentration exceeds that of 2-PGA by a factor of five to ten in the intact cell.

Results

Following incubation, the ATP and 2,3-DPG of the disinfected red blood cells (experiment) were compared with those of the untreated cells. These two enzymes are considered important predictors of the viability and suitability for transfusion of red blood cells.

No important difference in their ability to regenerate ATP and 2,3-DPG appeared. Results are displayed in Tables I and II. Both tables present concentrations obtained after disinfection, washing, protracted refrigeration, and incubation for the particular times tabulated.

Washing was in normal saline, and refrigeration was at four degrees Celsius as mentioned above. Incubations were performed at thirty-seven degrees Celsius, with the supplementation of glucose, inorganic phosphorus, potassium, and magnesium.

The experiments represented in Tables I and II differed principally in length of exposure to the disinfectant. Table I corresponds to the previously described disinfection period, less than one minute.

Table II data were taken following a disinfection period of four minutes—a stringent test of the ability of the cells to survive the disinfection step. Following four minutes of contact with the disinfectant, there was no evidence of hemolysis and no loss of ATP.

TABLE I

Red blood cell constituent concentrations (micromoles per gram hemoglobin) after described treatment, including disinfection for less than one minute

| Incubation time (hr.) | Control ATP | Control 2,3-DPG | Experiment ATP | Experiment 2,3-DPG |
|---|---|---|---|---|
| 0 | 0 | 0 | 0 | 0 |
| 2 | 1.79 | 0.96 | 1.34 | 2.89 |
| 4 | 1.19 | 0 | 1.34 | 0 |

TABLE II

Red blood cell constituent concentration (micromoles per gram hemoglobin) after described treatment, including disinfection for four minutes

| Incubation time (hr.) | ATP Control | ATP Experiment |
|---|---|---|
| 0 | 3.83 | 5.28 |
| 2 | 4.35 | 4.26 |

I therefore conclude that red blood cells are safe and suitable for human transfusion, following treatment as described herein. These red blood cells carry a much lessened risk or total absence of risk of transmitting the several harmful contaminants enumerated earlier, as well as other harmful contaminants not mentioned.

It will be understood that the foregoing disclosure is intended to be merely exemplary, and not to limit the scope of the invention—which is to be determined by reference to the appended claims.

I claim:

1. A method for reducing the infectivity of HIV-1 virus that causes AIDS; said method comprising the steps of:
   preparing a disinfectant from lactic acid and sodium chlorite, each in concentration of less than two percent, in a solution of normal saline;
   then exposing a substance comprising red blood cells to the disinfectant for a time period sufficient to inactivate HIV-1 virus; and
   then washing the red blood cells with normal saline until the concentration of disinfectant is insignificant.

2. The method of claim 1 wherein the concentration of lactic acid is from about $0.6 \times 10^{-3}$ to about 0.6 percent.

3. The method of claim 1 wherein the concentration of lactic acid is about $0.6 \times 10^{-2}$ percent.

4. The method of claim 1 wherein the concentration of sodium chlorite is from about $0.12 \times 10^{-3}$ to about 0.12 percent.

5. The method of claim 1 wherein the concentration of sodium chlorite is about $0.12 \times 10^{-2}$ percent.

6. The method of claim 1 wherein the exposing step is from one second to several minutes.

7. The method of claim 1 wherein the washing step and the exposing step is performed in an automatic cell washer.

8. A method for disinfecting red blood cells from HIV-1 virus, without harming said red blood cells, which comprises:
   a. contacting said red blood cells with a disinfectant, said disinfectant consisting essentially of an isotonic solution of chlorine dioxide in normal saline in an amount sufficient to inactivate HIV-1 virus present;
   b. allowing said disinfectant to remain in contact with the red blood cells for a period of time sufficient to inactivate HIV-1 virus, and;
   c. washing said red blood cells to substantially remove said disinfectant.

9. The method of claim 1 wherein said period of time is from one second to several minutes.

10. The method of claim 8 wherein the washing step further comprises washing with a hemolysis detering agent.

11. The method of claim 8 wherein the washing step further comprises washing with a solution isotonic with blood.

12. The method of claim 8 wherein the washing step further comprises washing with normal saline.

13. A method for disinfecting red blood cells from HIV-1 virus, without harming said red blood cells, which comprises:
   a. contacting said red blood cells with a disinfectant for a period of time sufficient to inactivate HIV-1 virus, said disinfectant consisting essentially of a normal saline solution of an acid and a water soluble chlorine dioxide liberating compound;
   b. washing said red blood cells to substantially remove said disinfectant.

14. The method of claim 13 wherein the acid is an inorganic acid selected from the group consisting of hydrochloric acid, sulfuric acid, and phosphoric acid.

15. The method of claim 13 wherein the acid is an organic acid selected from the group consisting of monocarboxylic acids and polycarboxylic acids containing from 2 to about 16 carbon atoms.

16. The method of claim 15 wherein the organic acid is selected from the group consisting of lactic acid, acetic acid, citric acid, sorbic acid, fumaric acid and tannic acid.

17. The method of claim 13 wherein the acid is at least 85% lactic acid.

18. The method of claim 13 wherein the acid is lactic acid.

19. The method of claim 13 wherein the water soluble chlorine dioxide liberating compound is sodium chlorite.

20. The method of claim 13 wherein the red blood cell washing step comprises washing in an automatic cell washer.

* * * * *